US008765970B2

(12) United States Patent
Antons et al.

(10) Patent No.: US 8,765,970 B2
(45) Date of Patent: Jul. 1, 2014

(54) PROCESS FOR PREPARING CHIRAL 3-TRIAZOLYL SULPHOXIDE DERIVATIVES

(71) Applicant: Bayer Intellectual Property GmbH, Monheim (DE)

(72) Inventors: Stefan Antons, Leverkusen (DE); Norbert Lui, Odenthal (DE); Wahed Ahmed Moradi, Monheim (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 13/652,039

(22) Filed: Oct. 15, 2012

(65) Prior Publication Data

US 2013/0172573 A1 Jul. 4, 2013

Related U.S. Application Data

(62) Division of application No. 12/837,646, filed on Jul. 16, 2010, now Pat. No. 8,314,133.

(30) Foreign Application Priority Data

Jul. 16, 2009 (DE) .......................... 10 2009 027 771

(51) Int. Cl.
*C07D 249/14* (2006.01)
(52) U.S. Cl.
USPC .................................... 548/263.8; 548/265.6
(58) Field of Classification Search
USPC .......... 514/383, 384; 548/263.8, 264.8, 265.6
See application file for complete search history.

(56) References Cited

U.S. PATENT DOCUMENTS

| 6,509,354 | B1 * | 1/2003 | Toriyabe et al. ............... 514/317 |
| 7,317,126 | B2 | 1/2008 | Rebiere et al. |
| 7,872,036 | B2 | 1/2011 | Toriyabe et al. |
| 8,314,133 | B2 | 11/2012 | Antons et al. |
| 2006/0281782 | A1 | 12/2006 | Cohen et al. |
| 2007/0299261 | A1 | 12/2007 | Cohen et al. |
| 2011/0053996 | A1 | 3/2011 | Andersch et al. |

FOREIGN PATENT DOCUMENTS

| CN | 101012141 A | 8/2007 |
| CN | 101429192 A | 5/2009 |
| EP | 1 076 053 A1 | 2/2001 |
| FR | 2 863 611 A1 | 6/2005 |
| FR | 2 876 101 A1 | 4/2006 |
| WO | WO 2006/040635 A1 | 4/2006 |

OTHER PUBLICATIONS

March, Advanced Organic Chemistry, 1992, 4th Ed. pp. 119-126.*
Bolm, C. and Bienewald, F., "Asymmetric Oxidation of Dithioacetals and Dithioketals Catalyzed by a Chiral Vanadium Complex," *SYNLETT* 12:1327-1328, Georg Thieme Verlag, Stuttgart, Germany (1998).
Bryliakov, K.P. and Talsi, E.P., "Transition Metal Catalyzed Asymmetric Oxidation of Sulfides," *Current Organic Chemistry* 12(5):386-404 , Bentham Science Publishers Ltd., Netherlands (2008).
Colombo, A., et al., "Chiral Induction in the Oxidation of Thioanisole With Chiral Oxotitanium(IV) Schiff Bases Complexes as Catalysts. The Importance of the Conformation of the Ligands," *Gazzetta Chimica Italiana* 116:35-40, Società Chimica Italiana, Italy (1986).
Colonna, S., et al., "Asymmetric Oxidation of Sulphides to Sulphoxides Catalysed by Titanium Complexes of N-Salicylidene-L-amino Acids," *J. Chem. Soc. Perkin Trans.* 1:71-73, London Chemical Society, England (1987).
Faber, K., "Biocatalytic Application" in *Biotransformations in Organic Chemistry: A Textbook, 3rd Edition*, pp. 222-225, Springer-Verlag, Germany (1997).
Fernández, I. and Khiar, N., "Recent Developments in the Synthesis and Utilization of Chiral Sulfoxides," *Chem. Rev.* 103:3651-3705, American Chemical Society, United States (2003).
Holland, H.L., "Biotransformation of organic sulfides," *Nat. Prod. Rep.* 18:171-181, The Royal Society of Chemistry, England (2001).
Kagan, H.B., "Asymmetric Oxidation of Sulfides," in *Catalytic Asymmetric Synthesis* 203-226, I. Ed. VCH, New York, United States (1993).
Noyori, R., "Asymmetric catalysis by chiral metal complexes," *Chemtech* 22:360-367, American Chemical Society, United States (1992).
Nugent, W.A., et al., "Beyond Nature's Chiral Pool: Enantioselective Catalysis in Industry," *Science* 259:479-483, American Association for the Advancement of Science, United States (1993).
Pitchen, P., et al., "An Efficient Asymmetric Oxidation of Sulfides to Sulfoxides," *J. Am. Chem. Soc.* 106:8188-8193, American Chemical Society, United States (1984).
Secundo, F., et al., "Asymmetric Oxidation of Sulfides by Cyclohexanone Monooxygenase," *Tetrahedron: Asymmetry* 4(9):1981-1982, Pergamon Press Ltd., England (1993).
Wu, Y., et al., "Vanadium-Catalyzed Asymmetric Oxidation of Sulfides Using Schiff Base Ligands Derived from β-Amino Alcohols with Two Stereogenic Centers," *Eur. J. Org. Chem.* 2607-2610, Wiley-VCH Verlag GmbH & Co. KGaA, Weinheim, Germany (2009).
Zeng, Q., et al., "Vanadium-Catalyzed Enantioselective Sulfoxidation and Concomitant, Highly Efficient Kinetic Resolution Provide High Enantioselectivity and Acceptable Yields of Sulfoxides," *Adv. Synth. Catal.* 347:1933-1936, Wiley-VCH Verlag GmbH & Co. KGaA, Weinheim, Germany (2005).
English language Abstract of Chinese Patent Publication No. CN 101012141 A, European Patent Office, espacenet database—Worldwide (2007).
English language Abstract of Chinese Patent Publication No. CN 101429192 A, European Patent Office, espacenet database—Worldwide (2009).
International Search Report for International Application No. PCT/EP2010/004288, European Patent Office, The Hague, Netherlands, mailed Oct. 5, 2010.
Office Action mailed on Aug. 2, 2012, in U.S. Appl. No. 12/836,696, inventors Andersch et al., filed Jul. 15, 2010.
Office Action mailed on Mar. 27, 2013, in U.S. Appl. No. 12/836,696, inventors Andersch et al., filed Jul. 15, 2010.

* cited by examiner

*Primary Examiner* — Rebecca Anderson
(74) *Attorney, Agent, or Firm* — Sterne, Kessler, Goldstein & Fox P.L.L.C.

(57) ABSTRACT

The present invention relates to a catalytic process for preparing 3-triazolyl sulphoxide derivatives in enantiomerically pure or enantiomerically enriched form.

4 Claims, No Drawings

PROCESS FOR PREPARING CHIRAL 3-TRIAZOLYL SULPHOXIDE DERIVATIVES

The present invention relates to a catalytic process for preparing 3-thiazolyl sulphoxide derivatives in enantiomerically pure or enantiomerically enriched form.

The chemical synthesis of 3-triazolyl sulphoxides is described in the literature, but leads to a racemic mixture (WO 1999/055668).

Enantiomerically pure chiral sulphoxides and corresponding derivatives are of great significance in the pharmaceutical and agrochemical industry. Such compounds can be processed further in order to provide exclusively the biologically active enantiomer of a medicament or chemical crop protection agent. This not only rules out waste in the preparation process but also avoids potentially harmful side effects which can arise from the undesired enantiomer (Nugent et al., *Science* 1993, 259, 479; Noyori et al., *CHEMTECH* 1992, 22, 360).

Enantioselective synthesis of chiral sulphoxides is described in the literature. Review articles which describe this methodology can be found, for example, in H. B. Kagan in "Catalytic Asymmetric Synthesis"; I. Ed. VCH: New York 1993, 203-226; Ojirna N. Khiar in *Chem. Rev.* 2003, 103, 3651-3705; K. P. Bryliakov in *Current Organic Chemistry* 2008, 12, 386-404. In addition to the conventionally metal-catalysed methods for synthesizing chiral sulphoxides, the literature also describes enzymatic and chromatographic processes (K. Kaber in "Biotransformations in Organic Synthesis", Springer Ed. 3rd ed. 1997; H. L. Holland, *Nat. Prod. Rep.*, 2001, 18, 171-181). The enzymatic methods are predominantly substrate-specific and, moreover, the industrial implementation is very costly and inconvenient. For example, monooxygenases and peroxidases are important enzyme classes which are capable of catalysing a multitude of sulphides to sulphoxides (S. Colonna et al., *Tetrahedron Asymmetry* 1993, 4, 1981). However, it has been found that the stereochemical result of the enzymatic oxidation depends greatly on the sulphide structure.

A frequently employed process for enantioselective oxidation of thioethers is the Kagan modification to the known method of sharpless epoxidation with chiral titanium complexes (*J. Am. Chem. Soc.* 1984, 106, 8188-8193). This involves "deactivating" the chiral titanium complex, consisting of Ti(OPr$^i$)$_4$ and (+)- or (−)-diethyl tartrate (DET) with one equivalent of water, and catalysing the enantioselective sulphide oxidation of arylalkyl sulphides. However, good results were achieved with the Kagan reagent with a Ti(OPr$^i$)$_4$/DET/H$_2$O mixing ratio=1:2:1 and an organic peroxide (e.g. tert-butyl hydroperoxide). The good enantioselectivity of the titanium complexes described is accompanied by a low catalytic activity, which describes the necessary ratio between substrate and catalyst. By means of this process, the direct oxidation of simple arylalkyl sulphides, for example arylmethyl sulphides, to optically active sulphoxides can be achieved. It has been found that the asymmetric oxidation of, for example, functionalized alkyl sulphides proceeds with moderate enantioselectivity under these conditions.

Pasini et al. were able to oxidize phenylmethyl sulphide with small amounts of chiral oxotitanium(IV) Schiff bases and hydrogen peroxide, but with poor enantiomeric excesses (ee-values <20%) (*Gaz. Chim. Ital.* 1986, 116, 35-40). Similar experiences are described by Colona et al. with chiral titanium complexes of N-salicyl-L-amino acids (*Org. Bioorg. Chem.* 1987, 71-71). In addition, titanium catalysed processes result in very complex workups, which is very disadvantageous for an economic process on the industrial scale.

A further method is based on vanadium(IV) Schiff bases as efficient catalysts for sulphide oxidation. The chiral catalyst is prepared in situ from VO(acac)$_2$ with a Schiff base of chiral amino alcohols (*Synlett* 1998, 12, 1327-1328; *Euro. J. Chem.* 2009, 2607-2610). However, this method is restricted to simple and nonfluorinated arylalkyl thioethers, for example p-tolylmethyl sulphide.

To date, the enantiomers of 3-triazolyl sulphoxides, which were obtained in racemic form by literature processes, were obtained by a complex separation by means of HPLC on chiral phases. The chromatographic separation of enantiomers or chiral stationary phases is, however, generally unsuitable for relatively large amounts of active ingredient, but serves merely for provision of relatively small amounts. Furthermore, utilization of HPLC on chiral phases is extremely costly especially on the preparative scale, owing to the high cost of these materials and the considerable investment of time.

There was therefore an urgent need for a catalytic process which is performable on the industrial scale in particular. It is therefore an object of the invention to provide such a catalytic process which, in addition to industrial implementability, ensures inexpensiveness, good yields and variation of the enantiomer ratio.

In view of the disadvantages and problems outlined above, there is an urgent need for a simplified, industrially and economically performable, catalytic process for enantioselective sulphide oxidation of substituted, fluorinated 3-triazolyl sulphoxide derivatives. The 3-triazolyl sulphoxide derivatives obtainable with this desired process should preferably be obtained with high yield and high purity. More particularly, the process desired should enable the desired target compounds to be obtained without the need for complex purification methods such as chiral chromatography.

The separation of the enantiomers and also the synthesis of 3-triazolyl sulphoxide derivatives which possess a chiral sulphoxide group in enantiomerically pure form or in an enantiomerically enriched form has not been described to date The object was achieved in accordance with the present invention by a process for preparing 3-triazolyl sulphoxide derivatives of the general formula (I),

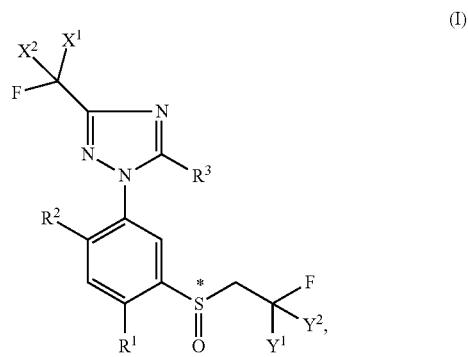

in which
X$^1$ and X$^2$ are each independently fluorine, chlorine, bromine, hydrogen, (C$_1$-C$_{12}$)alkyl, (C$_1$-C$_{12}$)haloalkyl,
Y$^1$ and Y$^2$ are each independently fluorine, chlorine, bromine, hydrogen, (C$_1$-C$_{12}$)alkyl, (C$_1$-C$_{12}$)haloalkyl,
R$^1$ and R$^2$ are each independently hydrogen, (C$_1$-C$_{12}$)alkyl, (C$_1$-C$_{12}$)haloalkyl, cyano, halogen, nitro,
R$^3$ is hydrogen, (C$_1$-C$_{12}$)alkyl, amino, nitro, NH(CO)(C$_1$-C$_{12}$)alkyl, N=CR'R where R, R' are each independently hydrogen, $(C_1-C_{12})$alkyl, aryl, characterized in that a sulphide of the formula (II)

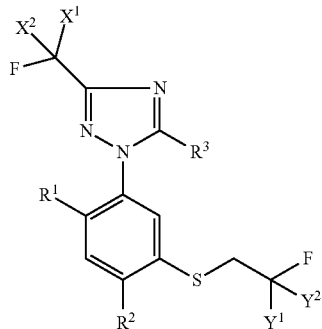

(II)

in which $X^1$, $X^2$, $Y^1$, $Y^2$, $R^1$, $R^2$ and $R^3$ are each as defined above is converted in the presence of a chiral catalyst and of an oxidizing agent.

Preferred, particularly preferred and very particularly preferred definitions of the $X^1$, $X^2$, $Y^1$, $Y^2$, $R^1$, $R^2$ and $R^3$ radicals shown in the abovementioned general formula (I) are elucidated hereinafter.

$X^1$, $X^2$, $Y^1$ and $Y^2$ are preferably each independently fluorine, chlorine, hydrogen, $(C_1-C_{12})$alkyl, $(C_1-C_{12})$haloalkyl, $R^1$ and $R^2$ are preferably each independently fluorine, chlorine, hydrogen, $(C_1-C_{12})$alkyl, $R^3$ is preferably hydrogen, $(C_1-C_{12})$alkyl, amino, $X^1$ and $X^2$, $Y^1$ and $Y^2$ are more preferably each independently fluorine, chlorine, hydrogen, $(C_1-C_{12})$haloalkyl, $R^1$ and $R^2$ are more preferably each independently fluorine, hydrogen, $(C_1-C_6)$alkyl, $R^3$ is more preferably hydrogen, amino, $X^1$ and $X^2$, $Y^1$ and $Y^2$ are most preferably each independently fluorine, hydrogen, $(C_1-C_6)$haloalkyl.

$R^1$ and $R^2$ are most preferably each independently fluorine, methyl, $R^3$ is most preferably hydrogen.

Surprisingly, the chiral 3-triazolyl sulphoxide derivatives of the formula (I) can be prepared under the inventive conditions with good yields in high purity, which means that the process according to the invention does not have the disadvantages described in connection with the prior art.

Compounds of the formula (I) form by the process according to the invention, according to the preparation conditions, in an enantiomer ratio of 50.5:49.5 to 99.5:0.5 (+):(−)-enantiomer or (−):(+)-enantiomer.

The enantiomeric purity can, if necessary, be increased by different processes. Such processes are known to those skilled in the art and include especially preferential crystallization from an organic solvent or a mixture of organic solvent with water.

The process according to the invention can be illustrated by the following scheme (I):

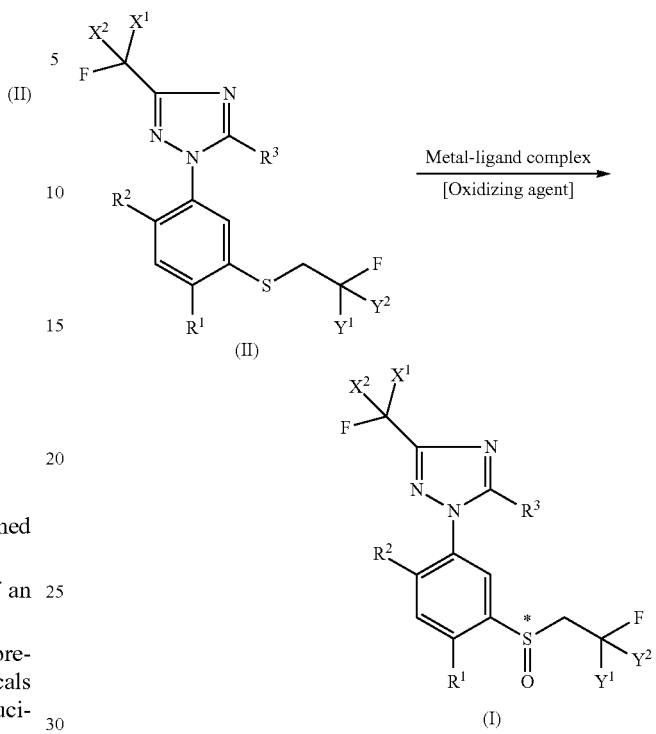

where $X^1$, $X^2$, $Y^2$, $R^1$, $R^2$, $R^3$ are each as defined above.

GENERAL DEFINITIONS

In the context of the present invention, the term "halogens" (Hal), unless defined differently, encompasses those elements which are selected from the group consisting of fluorine, chlorine, bromine and iodine, preference being given to using fluorine, chlorine and bromine and particular preference to using fluorine and chlorine.

Optionally substituted groups may be mono- or polysubstituted, and the substituents may be the same or different in the case of polysubstitutions.

Alkyl groups substituted by one or more halogen atoms (-Hal) are, for example, selected from trifluoromethyl ($CF_3$), difluoromethyl ($CHF_2$), $CF_3CH_2$, $ClCH_2$, $CF_3CCl_2$.

In the context of the present invention, alkyl groups, unless defined differently, are linear, branched or cyclic saturated hydrocarbon groups.

The definition "$C_1-C_{12}$-alkyl" encompasses the widest range defined herein for an alkyl group. Specifically, this definition encompasses, for example, the meanings of methyl, ethyl, n-, iso-propyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, aryl groups, unless defined differently, are aromatic hydrocarbon groups which may have one, two or more heteroatoms selected from O, N, P and S.

Specifically, this definition encompasses, for example, the meanings of cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, unless defined differently, alkylaryl groups are aryl groups which are substituted by alkyl groups and have an alkylene chain and may have, in the aryl skeleton, one or more heteroatoms selected from O, N, P and S.

The oxidizing agents which can be used for this reaction are not subject to any particular stipulations. It is possible to use oxidizing agents which are capable of oxidizing corresponding sulphur compounds to sulphoxide compounds. Suitable oxidizing agents for preparing the sulphoxides are, for example, inorganic peroxides, for example hydrogen peroxide, or organic peroxides, for example alkyl hydroperoxides and arylalkyl hydroperoxides. The preferred oxidizing agent is hydrogen peroxide. The molar ratio of oxidizing agent to the sulphide is in the range from 0.9:1 to 4:1, preferably between 1.2:1 and 2.5:1.

The chiral metal-ligand complex is prepared from a chiral ligand and a transition metal compound.

Transition metal derivatives are preferably vanadium derivatives, molybdenum derivatives, zirconium derivatives, iron derivatives, manganese derivatives and titanium derivatives, very preferably vanadium derivatives. These derivatives can be used, for example, in the form of the transition metal (IV) halides, transition metal(IV) alkoxides or transition metal(IV) acetylacetonates.

The chiral ligand is a chiral compound which is capable, for example, of reacting with the vanadium derivatives. Such compounds are preferably selected from chiral alcohols. Preferred chiral ligands likewise include Schiff bases of the formulae (III) and (IV):

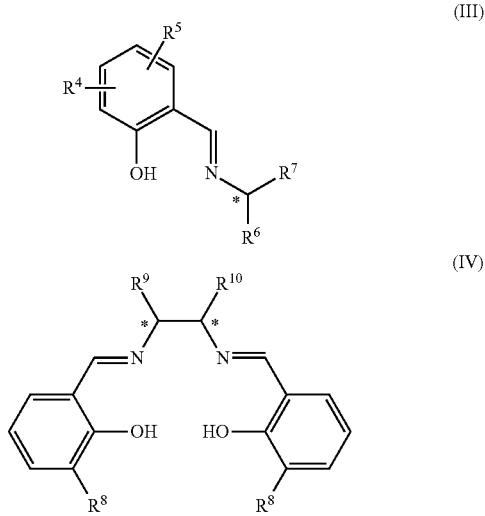

where, in formula (III),
$R^4$ and $R^5$ are each independently hydrogen, $(C_1-C_6)$alkyl, $(C_1-C_6)$alkylphenyl, phenyl, halogen, cyano, nitro, cyano$(C_1-C_6)$alkyl, hydroxy$(C_1-C_6)$alkyl, $(C_1-C_6)$alkoxycarbonyl$(C_1-C_6)$alkyl, $(C_1-C_6)$alkoxy$(C_1-C_6)$alkyl, $R^6$ is $(C_1-C_6)$alkyl, halogen-, cyano-, nitro-, amino-, hydroxyl- or phenyl-substituted $(C_1-C_6)$alkyl, carboxyl, carbonyl$(C_1-C_6)$alkyl, $(C_1-C_6)$alkoxycarbonyl$(C_1-C_6)$alkyl, $(C_1-C_6)$alkoxy$(C_1-C_6)$alkyl, $(C_1-C_6)$alkoxy, di$(C_1-C_6)$alkoxy$(C_1-C_6)$alkyl,
$R^7$ is hydrogen, $(C_1-C_6)$alkyl, $(C_1-C_6)$alkylphenyl, aryl, aryl $(C_1-C_6)$alkyl, preferably tert-butyl, benzyl, phenyl,
and chiral carbon atoms are designated *,
where, in formula (IV),
$R^8$ is hydrogen, $(C_1-C_6)$alkyl, $(C_1-C_6)$alkylphenyl, phenyl, halogen, cyano, nitro, cyano$(C_1-C_6)$alkyl, hydroxy$(C_1-C_6)$ alkyl, $(C_1-C_6)$alkoxycarbonyl$(C_1-C_6)$alkyl, $(C_1-C_6)$alkoxy $(C_1-C_6)$alkyl,
$R^9$ and $R^{10}$ are each hydrogen, $(C_1-C_6)$alkyl, phenyl, where $R^9$ and $R^{10}$ may form a bridge, and
chiral carbon atoms are designated *.

These Schiff bases can form a chiral metal-ligand complex, known as a chiral (salen)-metal complex. The stoichiometry of the chiral complexes may vary and is not critical to the invention.

The amount of the chiral metal-ligand complex used, compared to the sulphide, is in the range from 0.001 to 10 mol %, preferably from 0.1 to 5 mol %, most preferably 1 to 4 mol %. A higher use of chiral metal-ligand complex is possible but economically unviable.

The chiral transition metal complex is obtained by reaction of a transition metal derivative and a chiral complex ligand, separately or in the presence of the sulphide.

The conversion of the sulphide of the formula (II) to the compound with the formula (I) can be performed in the presence of a solvent. Suitable solvents include in particular: THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, ethyl acetate, isopropyl acetate, alcohols such as methanol, ethanol, propanol, butanol, ethylene glycol, ethylene carbonate, propylene carbonate, N,N-dimethylacetamide, N,N-dimethylformamide, N-methylpyrrolidone, halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; 4-methoxybenzene, fluorinated aliphatics and aromatics such as trichlorotrifluoroethane, benzotrifluoride, 4-chlorobenzotrifluoride, and water. It is also possible to use solvent mixtures.

It has additionally been observed that the enantiomer ratio can be controlled not only via the catalyst system but also via the solvent.

Further factors influencing the enantiomer ratio, as well as the oxidizing agent, also include the temperature.

Suitable methods for determining the enantiomeric excess are familiar to those skilled in the art. Examples include HPLC on chiral stationary phases and NMR studies with chiral shift reagents.

The reaction is generally performed at a temperature between −80° C. and 200° C., preferably between 0° C. and 140° C., most preferably between 10° C. and 60° C., and at a pressure up to 100 bar, preferably at a pressure between standard pressure and 40 bar.

The preparation of the thioethers of the general formula (II) is described, for example, in WO 1999/055668 or can be performed analogously.

The ligands are prepared by known processes (*Adv. Synth. Catal.* 2005, 347, 1933-1936).

The desired compounds of the general formula (I) can be isolated, for example, by subsequent extraction and crystallization.

The present invention is explained in detail by the examples which follow, though the examples should not be interpreted in such a manner as to restrict the invention.

Products obtained by the process according to the invention have an enantiomer ratio of 50.5:49.5 to 99.5:0.5, preferably of 60:40 to 95:5, more preferably of 75:25 to 90:10, (+):(−)-enantiomer or (−):(+)-enantiomer, most preferably (+):(−)-enantiomer. Therefore, preference is given in accordance with the invention to those enantiomer ratios within the ranges specified which have an excess of the (+)-enantiomer.

The enantiomeric excess may therefore be between 0% ee and 99% ee. The enantiomeric excess is an indirect measure of the enantiomeric purity of a compound and reports the proportion of a pure enantiomer in a mixture, the remaining portion of which is the racemate of the compound.

If required, a subsequent crystallization with or without solvent can considerably increase the enantiomeric excess. Such processes are known to those skilled in the art and include especially the preferred crystallization from an organic solvent or a mixture of organic solvent with water.

PREPARATION EXAMPLES

Example 1

Synthesis of (+)-1-{2,4-dimethyl-5-[(2,2,2-trifluoroethyl)sulphinyl]phenyl}-3-(trifluoromethyl)-1H-1,2,4-triazole In a three-neck flask, 10.3 g (27.54 mmol, 95% pure) of 1-{2,4-dimethyl-5-[(2,2,2-trifluoroethyl)sulphanyl]phenyl}-3-(trifluoromethyl)-1H-1,2,4-triazole and 145.8 mg (0.55 mmol) of vanadium acetylacetonate were dissolved in 36 ml of chloroform and stirred for 10 minutes. Subsequently, 275.8 mg (0.825 mmol) of (S)-(2,4-di-tert-butyl-6-{(E)-[(1-hydroxy-3,3-dimethylbutan-2-yl)imino]methyl}phenol were added. After 10 minutes, 5.66 g (50 mmol) of 30% $H_2O_2$ were metered in over 6 hours. The progress of the conversion was monitored by means of HPLC. After 4 h of reaction time, a further 145.8 mg (0.55 mmol) of vanadium acetylacetonate and 275.8 mg of (2,4-di-tert-butyl-6-{(E)-[(1-hydroxy-3,3-dimethylbutan-2-yl)imino]methyl}phenol in 4 ml of chloroform were metered in. Subsequently, 40 ml of chloroform, 20 ml of water and 20 ml of thiosulphate solution were added successively. After the aqueous phase had been removed, the organic phase was washed with water and dried over $Na_2SO_4$, and the solvent was evaporated under reduced pressure. This gave 10.84 g of grey-brown crystals of (+)-1-{2,4-dimethyl-5-[(2,2,2-trifluoroethyl)sulphinyl]phenyl}-3-(trifluoromethyl)-1H-1,2,4-triazole (98% yield, 93.1% HPLC purity) with 2.81% sulphone content. The enantiomeric excess was determined by means of HPLC on a chiral phase (Daicel Chiracel OJ-RH 150) with a ratio of 16.34:83.66.

The enantiomer ratio was improved, for example by crystallization from $CHCl_3$, to 3.39:96.61.

TABLE 1

Oxidation of 1-{2,4-dimethyl-5-[(2,2,2-trifluoroethyl)sulphanyl]phenyl}-3-(trifluoro-methyl)-1H-1,2,4-triazole under different conditions:

| Oxidizing agent | Solvent | Enantiomer ratio [(−):(+)] |
|---|---|---|
| $H_2O_2$ | $CHCl_3$ | 16.34:83.66 |
| $H_2O_2$ | $CHCl_3$ | 3.39:96.61 after crystallization from $CHCl_3$ |
| $H_2O_2$ | $CHCl_3$:toluene | 18.54:81.46 |
| tert-Butyl hydroperoxide | $CHCl_3$ | 50.0:50.0 |
| Cumene hydroperoxide | $CHCl_3$ | 50:50 |
| $H_2O_2$ | acetonitrile | 50:50 |
| $H_2O_2$ | DME | 31.49:68.51 |
| $H_2O_2$ | n-butanol | 36.61:63.39 |
| $H_2O_2$ | methanol | 50:50 |
| $H_2O_2$ | glacial acetic acid | 42.58:57.42 |
| $H_2O_2$ | EA | 35.18:64.82 |
| $H_2O_2$ | THF | 50:50 |
| $H_2O_2$ | Me—THF | 36.0:64.0 |
| $H_2O_2$ | 4-methoxybenzene | 16.33:83.67 |
| | 1,2-dichlorobenzene | 18.71:81.29 |
| $H_2O_2$ | chlorobenzene | 27.87:72.13 |
| $H_2O_2$ | 4-Cl-benzotrifluoride | 24.94:75.06 |
| $H_2O_2$ | 1,1,2,2-tetrachloroethane | 18.97:81.03 |
| $H_2O_2$ | DMAC | 46.78:53.22 |

TABLE 2

Oxidation of 1-{2,4-dimethyl-5-[(2,2,2-trifluoroethyl)sulphanyl]phenyl}-3-(trifluoro-methyl)-1H-1,2,4-triazole with different catalysts:

| Catalyst system | Oxidizing agent | Solvent | T | Enantiomer ratio [(−):(+)] |
|---|---|---|---|---|
| 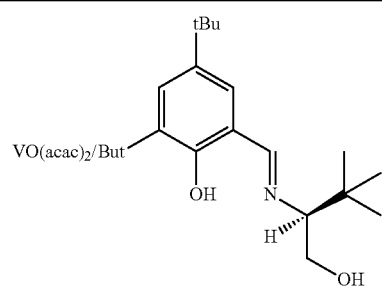 VO(acac)$_2$/But | $H_2O_2$ | $CHCl_3$ | RT | 16.34:83.66 |

TABLE 2-continued

Oxidation of 1-{2,4-dimethyl-5-[(2,2,2-trifluoroethyl)sulphanyl]phenyl}-3-(trifluoromethyl)-1H-1,2,4-triazole with different catalysts:

| Catalyst system | Oxidizing agent | Solvent | T | Enantiomer ratio [(−):(+)] |
|---|---|---|---|---|
| Fe(acac)$_3$/I 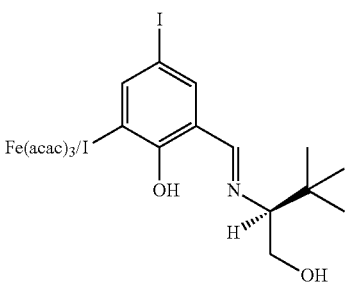 | H$_2$O$_2$ | DCM | RT | 18.04:81.96 |
| chiral 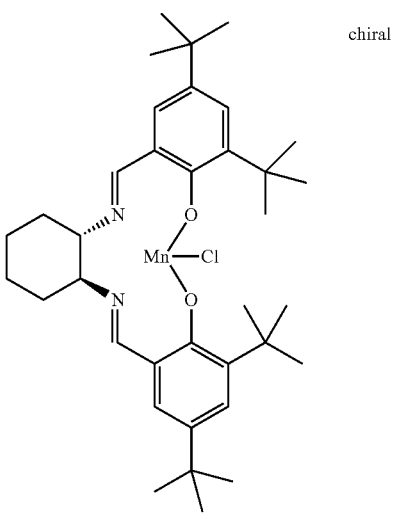 | H$_2$O$_2$ | acetonitrile | 40° C. | 19.91:80.09 |

Example 2

3-(Difluoromethyl)-1-{2,4-dimethyl-5-[(2,2,2-trifluoroethyl)sulphinyl]phenyl}-1H-1,2,4-triazole Analogously to Example 1,
3-(difluoromethyl)-1-{2,4-dimethyl-5-[(2,2,2-trifluoroethyl)sulphanyl]phenyl}-1H-1,2,4-triazole was used to obtain 3-(difluoromethyl)-1-{2,4-dimethyl-5-[(2,2,2-trifluoroethyl)sulphinyl]phenyl}-1H-1,2,4-triazole. The enantiomeric excess was determined by means of HPLC on a chiral phase (Daicel Chiracel OJ-RH 150) with a ratio of 7.37:92.63.

Example 3

1-{5-[(2,2-Difluoroethyl)sulphinyl]-2,4-dimethylphenyl}-3-(difluoromethyl)-1H-1,2,4-triazole Analogously to Example 1, 1-{5-[(2,2-difluoroethyl)sulphanyl]-2,4-dimethylphenyl}-3-(difluoro-methyl)-1H-1,2,4-triazole was used to obtain 1-{5-[(2,2-difluoroethyl)sulphinyl]-2,4-dimethylphenyl}-3-(difluoromethyl)-1H-1,2,4-triazole. The enantiomeric excess was determined by means of HPLC on a chiral phase (Daicel Chiracel OJ-RH 150) with a ratio of 19.97:80.03.

The invention claimed is:

1. An enantiomerically enriched 3-triazolyl sulphoxide of formula (I),

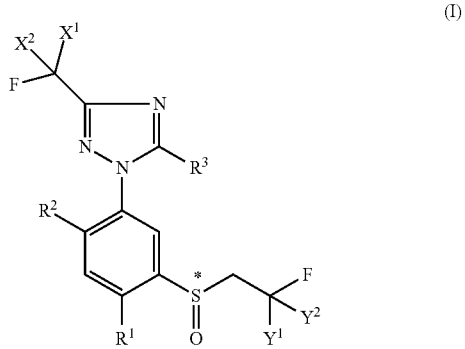

(I)

wherein
$X^1$ and $X^2$, $Y^1$ and $Y^2$ are each independently selected from the group consisting of fluorine, hydrogen, and (C$_1$-C$_6$) haloalkyl,
$R^1$ and $R^2$ are each independently selected from the group consisting of fluorine, and methyl, and
$R^3$ is amino, where the enantiomer ratio is 60:40 to 99.5:0.5 (+):(−) enantiomer,
and wherein said 3-triazolyl sulphoxide of formula (I) is prepared by a process comprising reacting a sulphide of formula (II)

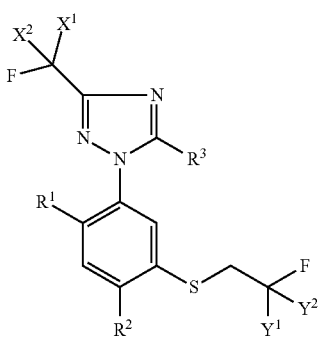

in which
each of $X^1$, $X^2$, $Y^1$, $Y^2$, $R^1$, $R^2$ and $R^3$ is as defined above,
with an oxidizing agent, in a solvent, and in the presence of a chiral catalyst, at a reaction temperature between 10° C. and 60° C.,
wherein the oxidizing agent is hydrogen peroxide; and the chiral catalyst is a chiral metal-ligand complex comprising a transition metal and a chiral ligand, wherein the transition metal is vanadium, iron or manganese.

2. The 3-triazolyl sulphoxide of formula I according to claim 1, wherein the enantiomer ratio is 75:25 to 90:10 (+):(−)enantiomer.

3. The 3-triazolyl sulphoxide of formula I according to claim 1, wherein the enantiomer ratio is 60:40 to 95:5 (+):(−) enantiomer.

4. The 3-triazolyl sulphoxide of formula (I) according to claim 1,
in which
$X^1$ and $X^2$, $Y^1$ and $Y^2$ are each independently selected from the group consisting of fluorine, and hydrogen.

* * * * *